US007943353B2

(12) United States Patent
Yu et al.

(10) Patent No.: US 7,943,353 B2
(45) Date of Patent: May 17, 2011

(54) MULTI-LAYER CELL ENCAPSULATION FOR TISSUE ENGINEERING

(75) Inventors: Hanry Yu, Irvine, CA (US); Kam W Leong, Ellicot City, MD (US); Ser-Mien Chia, Singapore (SG); Andrew C. A. Wan, Singapore (SG)

(73) Assignees: Agency for Science, Technology and Research, Centros (SG); The National University of Singapore, Singapore (SG)

( * ) Notice: Subject to any disclaimer, the term of this patent is extended or adjusted under 35 U.S.C. 154(b) by 0 days.

(21) Appl. No.: 12/507,900

(22) Filed: Jul. 23, 2009

(65) Prior Publication Data

US 2009/0286278 A1 Nov. 19, 2009

Related U.S. Application Data

(62) Division of application No. 11/137,483, filed on May 26, 2005, now abandoned, which is a division of application No. 09/975,273, filed on Oct. 12, 2001, now Pat. No. 6,916,640.

(60) Provisional application No. 60/239,259, filed on Oct. 12, 2000.

(51) Int. Cl.
*C12N 11/04* (2006.01)

(52) U.S. Cl. ... 435/182; 435/177; 435/180; 427/213.34; 514/963

(58) Field of Classification Search .................. None
See application file for complete search history.

(56) References Cited

U.S. PATENT DOCUMENTS

| | | | |
|---|---|---|---|
| 3,959,078 A | 5/1976 | Guire | |
| 4,293,654 A | 10/1981 | Levine | |
| 4,743,545 A | 5/1988 | Torobin | |
| 4,798,786 A | 1/1989 | Tice | |
| 4,994,388 A | 2/1991 | Hillegas | |
| 5,620,883 A | 4/1997 | Shao | |
| 5,833,979 A | 11/1998 | Schinstine | |
| 5,837,234 A | 11/1998 | Gentile | |
| 5,840,576 A | 11/1998 | Schinstine | |
| 5,846,952 A | 12/1998 | Vournakis | |
| 5,853,717 A | 12/1998 | Schinstine | |
| 5,858,350 A | 1/1999 | Vournakis | |
| 5,858,747 A | 1/1999 | Schinstine | |
| 5,908,623 A | 6/1999 | Baetge | |

FOREIGN PATENT DOCUMENTS

| | | |
|---|---|---|
| EP | 0222718 | 5/1987 |
| EP | 0529751 | 2/1993 |
| WO | 9107485 | 5/1991 |

OTHER PUBLICATIONS

Lai et al., "Membrane Fluidity of Chinese Hamster Ovary Cells on Plasma Fibronectin-coated Microcarriers", Experimental Cell Research, vol. 150, Issued 1984, pp. 78-79.
Pierschbacher et al., "Cell Attachment Activity of Fibronectin can be duplicated by Small Synthetic fragments of molecule", Nature, vol. 309, Issued May 3, 1984, pp. 30-33.
Hu et al., "Cultivation of Mammalian Cells in Bioreactors", Biotechnology Process, vol. 1, No. 4, issued Dec. 1985, pp. 209-215.
Van Wezel, "Growth of Cell-Strains and Primary Cells on Microcarriers in Homogeneous Culture", Nature, vol. 216, issued Oct. 7, 1967, pp. 64-65.
Varani et al., "Cell Growth on Microcarriers: Comparison of Proliferation on and recovery from various substances", Journal Biological Standardization, vol. 14, pp. 331-336, 1986.
Pharmacia Fine Chemicals, "Microcarrier Cell Culture", published Dec. 1981, pp. 1-33, and 121-127.
Chia et al, Biomaterials, 2002, vol. 23, No. 3, p. 849-56.
Koster, J., The Integrin page, 1997, assessed Sep. 2004. http://Integrins.hypermart.net/index/html.
Ishikawa, O., Kondo, A., Okada, K., Miyachi, Y., and Furumura, M., British Journal of Dermatology, Morphological and biochemical analyses on fibroblasts and self-produced collagens in a novel three-dimensional culture, 1997: 136: pp. 6-11.
Puviani, A.C., Lodi, A., Tassinari, B., Ottolenghi, C., Ganzerli, S., Ricci, D., Pazzi, P., and Morsiani, E., The International Journal of Artificial Organs, Morphological and functional evaluation of isolated rat hepatocytes in three dimensional culture systems, vol. 22, No. 11, 1999, pp. 778-785.
Cappai, A., Petruzzo, P., Ruiu, G., Congui, T., Dessy, E., De Seta, W., Santa Cruz, G, and Brotzu, G., The International Journal of Artificial Organs, Evaluation of new small barium alginate microcapsules, vol. 18, No. 2, 1995, pp. 96-102.
Konur, Abdo, Kreutz, Marina, Knüchel, Ruth, Krause, Stefan W., and Andreesen, Reinhard, International Union Against Cancer Journal, Three-Dimensional Co-Culture of Human Monocytes and Macrophages with Tumor Cells: Analysis of Macrophage Differentiation and Activation, 66, pp. 645-652, 1996.
Zekorn, T., Endl, A., Horcher, A., Siebers, U., Bretzel, R.G., and Federlin, K., Transplantation Proceedings, Mixed Lymphocyte Islet Culture for Assessment of Immunoprotection by Islet Microencapsulation, vol. 27, No. 6, Dec. 1995, pp. 3362-3363.
Kunz-Schughart, Leoni A., Kreutz, Marina, and Knuechel, Ruth, International Journal of Experimental Pathology, Multicellular spheroids: a three-dimensional in vitro culture system to study tumour biology, 1998, 79, pp. 1-23.

(Continued)

*Primary Examiner* — Allison M Ford
(74) *Attorney, Agent, or Firm* — Banner & Witcoff, Ltd.

(57) ABSTRACT

A multi-layered microcapsule has an inner extracellular matrix and an outer shell. The inner extracellular matrix includes a first inner layer of biopolymer and a second intermediate layer of polymer that provides partial immune-protection and holds the first layer in place. The outer shell can form an exoskeleton to provide mechanical stability. Each of the individual layers can be varied to optimize mechanical stability, cell function, and immuno-protection.

19 Claims, 3 Drawing Sheets

OTHER PUBLICATIONS

Kaufmann, P.M., Heimrath, S., Kim, B.S., and Mooney, D.J., Elsevier Science Inc., Cell Transplantation, Highly Porous Polymer Matrices as a Three-Dimensional Culture System for Hepatocytes, vol. 6, No. 5, pp. 463-468, 1997.

Weber, Collin J., Hagler, Mary K., Chryssochoos, John T., Kap, Judith A., Korbutt, Gregory S., Rajotte, Ray V., and Linsley, Peter S., Elsevier Science Inc., Cell Transplantation, CTLA4-1g Prolongs Survival of Microencapsulated Neonatal Porcine Islet Xenografts in Diabetic NOD Mice, vol. 6, No. 5, pp. 505-508, 1997.

Wang, W.J., Inoue, K., Hayashi, H., Aung, T., Tun, T., Gu, Y.J., Kaji, H., Echigo, Y., Kato, M., Doi, R., Setoyama, H., Kawakami, Y., Imamura, M., Maetani, S., Morikawa, N., Iwata, H., Ikada, Y., and Miyazaki, J.I., Transplantation Proceedings, Efficacy of Microencapsulation of a Pancreatic B-Cell Line (MIN6) in an Agarose/PPSa Microbead as a Bioartificial Pancreas, vol. 28, No. 2, Apr. 1996, pp. 1094-1096.

Pueyo, M.E., Darquy, S., Arbet-Engels, C., Poitout, V., Di Maria, S., Gangnerau, M.N., and Reach, G., The International Journal of Artificial Organs, A Method for obtaining monodispersed cells from isolated porcine islets of Langerhans, vol. 18, No. 1, 1995, pp. 34-38.

Woods, Erik J., Liu, Jun, Zieger, Michael A.J., Lakey, Jonathan R.T., and Critser, John K., Cell Transplantation, The Effects of Microencapsulation on Pancreatic Islet Osmotically Induced Volumetric Response, vol. 8, pp. 699-708, 1999.

Ao, Z., Korbutt, G.S., Warnock, G.L., Flashner, M., Colby, C.B., Luskey, K.L., and Rajotte, R.V., Transplantation Proceedings, Microencapsulation Improves Canine Islet Survival In Vivo, vol. 27, No. 6, Dec. 1995, pp. 3349-3350.

Bishop, J.R.P., Nelson, G., and Lamb, J., J. Microencapsulation, Microencapsulation in yeast cells, vol. 15, No. 6, 1998, pp. 761-773.

Kyle, Alastair H., Chan, Carmel T.O., and Minchinton, Andrew I., Bioplysical Journal, Characterization of Three-Dimensional Tissue Cultures Using Electrical Impedance Spectroscopy, vol. 76, May 1999, pp. 2640-2648.

Lakey, Jonathan R.T., Cavanagh, Thomas J., Zieger< Michael A.J., and Wright, MaryJo, Elsevier Science, Inc., Cell Transplantation, Evaluation of a Purified Enzyme Blend for the Recovery and Function of Canine Pancreatic Islets, vol. 7, No. 4, pp. 365-372, 1998.

Hsu, Brend Ray-Sea, Chnag< Fu-Hsiung, Juang, Jyuhn-Huarng, Huang, Yu-Yao, and Fu, Shin-Huei, Cell Transplantation, The Rescue Effect of 15-Deoxyspergulin on Intraperitoneal Microencapsulated Xenoislets, vol. 8, pp. 307-315, 1999.

Bruni, S. and Chang, T.M.S., The International Journal of Artificial Organs, Effect of donor strains and age of the recipient in the use of microencapsulated hepatocytes to control hyperbilirubinemia in the Gunn rat, vol. 18, No. 5, 1995, pp. 332-339.

Takeshita, Kazuyoshi, Ishibashi, Haruaki, Suzuki, Masayuki, Yamamoto, Takumi, Akaike, Toshihiro, and Kodama, Masashi, Artificial Organs, High Cell-Density Culture System of hepatocytes Entrapped in a Three-Dimensional Hollow Fiber Module with Collagen Gel, vol. 19, No. 2, pp. 191-193, 1995.

Chandy, Thomas, Moorandian, Daniel L., and Rao, Gundu H.R., Artificial Organs, Evaluation of Modified Alginate-Chitosan-Polyethlene Glycol Microcapsules for Cell Encapsulation, vol. 23, No. 10, pp. 894-903, 1999.

Jork, A., et al, Appl Microbiol Biotechnol, Biocompatible alginate from freshly collected *Laminaria pallida* for implantation, vol. 53, pp. 224-229, 2000.

Robitaille, et al. Studies on small (<350 μm) alginate-poly-L-lysine microcapsules. III. Biocompatibility of smaller versus standard microcapsules, pp. 116-120, 1999, J Biomed Mater Res.

De Vos, et al. Diabetes, Why Do Microencapsulated Islet Grafts Fail in the Absence of Fibrotic Overgrowth?, vol. 48, pp. 1381-1388, Jul. 1999.

Spancake, et al., Cancer Research, E7-transduced Human Breast Epithelial Cells Chow Partial Differentiation in Three-dimensional Culture, vol. 59, pp. 6042-6045, Dec. 15, 1999.

Acartürk, F. and Takka, S., J. Microencapsulation, Calcium alginate microparticles for oral administration: I effect of sodium alginate type drug release and drug entrapment efficiency, vol. 16, No. 3, pp. 291-301, 1999.

Takka, S. and J Acartürk, F., J. Microencapsulation Calcium alginate microparticles for oral administration: II effect of formulation factors on drug release and drug entrapment efficiency, vol. 16, No. 3, pp. 275-290, 1999.

Cruise, et al. Biotechnology and Bioengineering, A Sensitivity Study of the Key Parameters in the Interfacial Photopolyerization of Poly(ethyleneglycol) Diacrylate upon Porcine Islets, vol. 57, No. 6, Mar. 20, 1998, pp. 655-665, 1998.

Machluf, et al. World J Urol, Controlled release of therapeutic agents: slow delivery and cell encapsultaion, vol. 18, pp. 80-83, 2000.

Chang, et al. TIBTECH, in vivo delivery of heterologous proteins by microencapsulated recombinant cells, vol. 17, pp. 78-83, Feb. 1999.

Yu, et al., Transplantation Proceedings, Fructose Protects Rat Hepatocytes Against Hypoxic Injury During the Process of Isolation and Microencapsulation, vol. 31, pp. 1080-1083, 1999.

Lanza, et al., J Mol Med, Transplantation of islets using microencapsulation: studies in diabetic rodents and dogs, Vo. 77, pp. 206-210, 1999.

Van Schilfgaarde, et al. J Mol Med, Factors influencing the properties and performance of microcapsules for immunoprotection of pancreatic islets, vol. 77, pp. 199-205, 1999.

Zekorn, et al J Mol Med, Synergistic effect of microencapsulation and immunoalteration on islet allograft survival in bioartificial pancreas, vol. 77, pp. 193-198, 1999.

Peirone, et al. Encapsulation of various recombinant mammalian cell types in different alginate microcapsules, pp. 587-596, 1998, J Biomed Mater Res.

Kuzuya, et al., Experimental Cell Research, Induction of Apoptotic Cell Death in Vascular Endothelial Cells Cultured in Three-Dimensional Collagen Lattice, vol. 248, pp. 498-508, 1999.

Gómez-Lechón, et al. Journal of Cellular Phsiology, Long-Term Expression of Differentiated Functions in Hepatocytes Cultured in Three-Dimensional Collagen Matrix, vol. 177, pp. 553-562, 1998.

Garfinkel, et al. Journal of Surgical Research, Optimization of the Microencapsulated Islet for Transplantation, vol. 76, pp. 7-10, 1998.

Campioni, et al. HEMA/MMMA microcapsule implants in hemiparkinsonian rat brain: biocompatibility assessment using {3H}PK11195 as a marker for gliosis, Biomaterials, vol. 19, pp. 829-837, 1998.

Tashiro, et al. Transplantation Proceedings, Microencapsulation Improves Viability of Islets Form CSK Miniature Swine, vol. 30, p. 491, 1998.

Hisano, et al. Entrapment of islets into reversible disulfide hydrogels, pp. 115-123, 1998, J Biomed. Mater. Res.

Maysinger, et al. TIBTECH, Drug delivery to the nervous system, vol. 15, pp. 410-418, Oct. 1997.

Korbutt, et al. Transplantation Proceedings, Microencapsulation of Neonatal Porcine Islets: Long-Term Reversal of Diabetes in Nude Mice and In Vitro Protection From Human Complement Mediated Cytolysis, vol. 29, p. 2128, 1997.

De Vos, P., De Haan, B.J., Wolters, G.H.J., Strubbe, J.H., and Van Schilfgaarde, R., Springer-Verlag, Diabetologia, Improved biocompatibility but limited graft survival after purification of alginate for microencapsulation of pancreatic islets, vol. 40, pp. 262-270, 1997.

Hammond PT, "Recent explorations in electrostatic multilayer thin film assembly," Current Opinion in Colloid & Interface Science, vol. 4, Issue 6, Dec. 1, 1999, pp. 430-442.

MULTI-LAYER CELL ENCAPSULATION FOR TISSUE ENGINEERING

CROSS-REFERENCE TO RELATED APPLICATION

This application is a divisional application of U.S. application Ser. No. 11/137,483, filed Oct. 12, 2001, pending, which is a divisional application of U.S. application Ser. No. 09/975,273, filed Oct. 12, 2001, now patented (U.S. Pat. No. 6,916,640), which claims benefit under 35 U.S.C. §119(e) to U.S. application Ser. No. 60/239,259, filed Oct. 12, 2000, the disclosure of each of which is hereby incorporated by reference in its entirety.

BACKGROUND OF THE INVENTION

1. Field of the Invention

This invention relates to cell encapsulation and, more particularly, to encapsulating living cells in a multi-layer polymeric membrane.

2. Description of Related Art

Microcapsules for biological substances are composed of thin, semi-permeable membranes of cellular dimensions. Microcapsules can be prepared of various polymers and their contents can consist of enzymes, cells and other biological materials. Microcapsules are prepared in such a way as to prevent their contents from leaking out and causing an immunological reaction, but the microcapsules still allow the nutrients and metabolites to exchange freely. This method has found applications primarily in transplantation of foreign materials in vivo without immunosuppression. One example is microencapsulation of hepatocytes for use in bio-assisted liver devices (BLAD). The surface-to-volume ratio of a spherical microcapsule facilitates maximal transport of nutrients, gases, or metabolites exchange across the membrane. In addition, encapsulation of living cells allows better control of the microenvironment for optimal cellular functions via selection of suitable substrate and incorporation of controlled-release features into the local microenvironment. Other physical characteristics such as mass transport, mechanical and chemical stability can also be configured as desired without drastically affecting the functions of the living cells inside the microcapsules.

The commonly used techniques for cell encapsulation are complex coacervation and interfacial precipitation. Complex coacervation involves the electrostatic interaction of two oppositely charged polyelectrolytes. At the right matching charge density, the two poly-ions combine and migrate to form a colloid-rich or water-insoluble phase. The molecular weight and chain conformation parameters of the poly-ions may also play an important role in the complexation process. Interfacial precipitation simply relies on the solidification of a dissolved polymer upon contact with an aqueous phase.

One of the most extensively studied cell encapsulation schemes is one that involves an alginate-gelation complex coacervation method. In this system, alginate, a glycuranan extracted from the brown seaweed algae, can be chelated by calcium or other multivalent counter-ions to form a gel. These early in vivo results with the alginate-polylysine system have not been consistent because of the uncontrolled purity of alginate, and the incorporation of cells into the external membrane. As a result, a 2-step encapsulation was developed to further shield sensitive cells from the extra-capsular environment. The living cells were mixed with sodium alginate and extruded into calcium chloride to form calcium alginate gel droplets. These gel droplets were incorporated into larger alginate gel spheres and then reacted with a poly-amino acid such as poly-L-lysine to form a semi-permeable membrane. Incubating with sodium citrate liquefied the interior to form microcapsules. Unfortunately, the addition of sodium citrate appears to have affected the functions of the cells. Furthermore, the water-soluble alginate and poly-lysine were shown to be not particularly biocompatible as individual polymers, other matrices such as collagen may be better substrates for cellular functions than alginate.

To encapsulate living cells in natural matrices such as collagen, interfacial precipitation has been used. In this method, hydroxylethyl methacrylate-methylmethacrylate (HEMA-MMA) solution in dimethyl formamide and cell-suspension in collagen or Matrigel were extruded separately through two concentrically configured needles into a precipitating bath containing largely water with a floating layer of dodecane. Polyacrylates are water insoluble that enhances the in vivo stability of the microcapsules. The living cells encapsulated this way (especially with Matrigel) survive well. The interfacial precipitation requires a more elaborate setup than the complex coacervation to control the microcapsule sizes and minimize the contact of cells with organic solvents.

In U.S. application Ser. No. 09/414,964, filed Oct. 12, 1999, a negatively charged ter-polymer of hydroxyethyl methacrylate-methyl methacrylate-methacrylic acid (HEMA-MMA-MAA) is used to encapsulate cells within a positively charged collagen. The MAA added into the ter-polymer enhances the water solubility of the polymer, allowing the entire encapsulation to be carried out in an aqueous environment. Hence, the complex coacervation method is used while a simple setup provides for easy control of the microcapsule size. The resulting hepatocyte microcapsules exhibit enhanced cellular functions as well as desirable physical characteristics for use in bio-artificial liver. The microcapsules, however, were mechanically unstable as measured by nano-indentation method. After 4 days of static in vitro culture, the microcapsules became weak and breakable upon harsh handling. Attempts at improving the mechanical stability of the microcapsules resulted in tradeoffs with immune-barrier/mass transfer efficiencies and cellular function.

There remains a need for improved microcapsules that exhibit satisfactory mechanical stability in combination with improved immune-barrier/mass transfer efficiencies and cellular function.

SUMMARY OF THE INVENTION

The present invention, according to one aspect, is directed to a microcapsule for culturing cells, particularly anchorage-dependent cells. An inner, extra-cellular matrix surrounds the cells. The inner extracellular matrix can be formed from a biopolymer inner layer and a biocompatible synthetic polyelectrolyte outer layer, wherein the inner layer and the outer layer have charges sufficient to form a complex of the biopolymer and the polyelectrolyte. An outer shell of synthetic polymer surrounds and supports the extracellular matrix. The microcapsules are permeable to nutrients necessary to sustain normal metabolic functions of the cells and to toxins released by the cells.

According to another embodiment, a microcapsule for culturing anchorage-dependent cells comprises an inner extra-cellular matrix surrounding the cells and an outer shell surrounding and supporting the extracellular matrix. The outer shell comprises a macro-porous exoskeleton formed by complex coacervation with the extracellular matrix. The macro-porous exoskeleton preferably includes such biocompatible materials as alumina, alumina sol, or chitosan.

According to yet another embodiment, a microcapsule comprises an inner extracellular matrix surrounding living cells, a macro-porous exoskeleton surrounding and supporting the extracellular matrix, and an outer shell of synthetic polymer surrounding the macro-porous exoskeleton.

The microcapsule membrane preferably is permeable to molecules smaller than or equal to the size of albumin, to nutrients necessary to sustain normal metabolic functions of the bioactive cells, and to toxins released by the bioactive cells. The microcapsule membrane preferably is impermeable to immunoglobulins and macrophages.

The multi-layered microcapsule of the present invention systematically addresses all the major aspects of the microencapsulation development: optimal ECM environment for high cell functions, good mechanical stability, and reliable immune-protection. Most previous efforts have been focused on immune-barrier development while keeping cell viability only. In most cases, cell functions were quite poor. For hepatocyte encapsulation, cell functions never exceeded that exhibited by the monolayer culture control. While some other microcapsules do exhibit good mechanical stability, the cell functions and mass transfer properties have been unsatisfactory. Therefore, the enhancement of cell functions due to encapsulation was not fully exploited; the mechanical stability was weak; and effective immune-barrier could not be ensured. The multi-layered cell encapsulation of the invention advantageously allows all three major properties of the microcapsules to be systematically tuned for required applications in tissue engineering.

BRIEF DESCRIPTION OF THE DRAWINGS

The present invention will now be described in more detail with reference to preferred embodiments of the invention, given only by way of example, and illustrated in the accompanying drawings in which:

FIG. 2A is a scanning micrograph of a Type-III microcapsule using 0.02% chitosan as the exoskeleton biomaterial, and FIG. 2B is a scanning micrograph of a Type-III microcapsule using 6 mM alumina sol-gel as the exoskeleton material, illustrating a macro-porous network formed by the condensation of positively charged alumina particles on the exterior of the microcapsule (scale bars represent 10 μm);

DETAILED DESCRIPTION OF THE INVENTION

Figure 1:
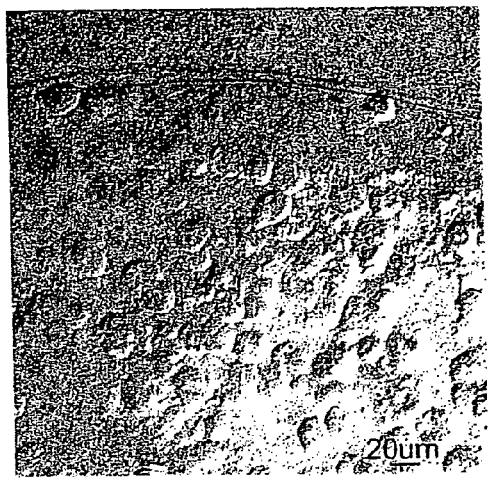
FIG. 1 is a confocal micrograph of a Type-II microcapsule, which illustrates that the second ter-polymer shell covers the cells protruding from the inner ter-polymer shell to ensure a more thorough encapsulation.

A multi-layer microcapsule comprises an extracellular matrix having bioactive cells attached to a microcapsule membrane. The microcapsule membrane has a first inner layer of biopolymer, such as cationic collagen, anionic collagen, anionic esterified hyaluronic acid, or anionic amine-modified hyaluronic acid, and a second intermediate layer of polyelectrolyte synthetic polymer. As described herein, the microcapsule also has an outer shell to improve mechanical stability. The microcapsule may include additional layers, such as a fourth outermost layer of polyelectrolyte synthetic polymer. The layers can be individually tailored to meet the needs of a particular application.

As used herein, "Type-I microcapsule" refers to cells within a biopolymer, such as a positively charged collagen, encapsulated with a polyelectrolyte synthetic polymer, such as a negatively charged ter-polymer of hydroxyethyl methacrylate-methyl methacrylate-methacrylic acid (HEMA-MMA-MAA). Such microcapsules are described in U.S. application Ser. No. 09/414,964, filed Oct. 12, 1999, the disclosure of which hereby is incorporated by reference.

"Type-II microcapsule," as used herein, refers to a microcapsule prepared by re-encapsulating a Type-I microcapsule in biopolymer- and polyelectrolyte synthetic polymer solutions.

"Type-III microcapsule," as used herein, refers to a microcapsule prepared by re-suspending a Type-I microcapsule in an exoskeleton material to form a macro-porous network.

"Type-IV microcapsule," as used herein, refers to a microcapsule prepared by re-encapsulating a Type-III microcapsule in a polyelectrolyte synthetic polymer solution.

Both naturally-occurring and modified biopolymers are suitable for use as biopolymers in the practice of the invention, as are both cationic and anionic biopolymers. In general, any commonly used substrates in cell studies can be used, non-limiting examples of which include collagen, cationic collagen, anionic collagen, anionic esterified hyaluronic acid, anionic amine-modified hyaluronic acid, fibronectin, and laminin. The biopolymers preferably are water-soluble and most often have a molecular weight of at least 20,000, preferably at least 75,000, more preferably at least 125,000, even more preferably at least 200,000, and yet even more preferably at least 250,000.

Whereas collagen has been used to encapsulate drugs, it has not found widespread use for encapsulating cells because, at neutral pH, there is insufficient charge density to form an encapsulating membrane. However, collagen modified to raise its pKi to at least about 9 is sufficiently positively charged at physiological pH to be complexed with oppositely-charged synthetic polyelectrolytes to form a coherent membrane. Collagen can be modified to form a more strongly basic polymer by converting the primary amino groups to tertiary amine groups or by esterification.

Anionic biopolymeric materials, such as hyaluronic acid (HA) and modified HA (esterified HA or amine-modified HA) are useful in the invention. In general, anionic biopolymers suitable for the practice of this invention will have a charge density of at least about 20%, preferably at least about 30%, and even more preferably at least about 50%. HA that is totally or partially esterified or reacted with a primary amine to render it less water-soluble will form a stronger complex with the polycationic outer layer than HA itself.

Preferred biopolymers for forming the inner layer of the encapsulating membrane are modified HA and modified collagen. Esterified collagen is particularly preferred as the inner layer. In general, the inner layer, though water-soluble, will be slightly hydrophobic.

Esterification or reaction to form tertiary amine groups on the biopolymer may be accomplished by reaction of the biopolymer with a wide variety of aliphatic reactants containing as many as about 18 carbon atoms in their chain. Such reactants include, inter alia, alcohols, primary amines and alcohol amines. Preferred reactants contain about 8 carbon atoms or less. For some purposes, use of reactants having only 2 or 3 carbon atoms may be preferred. Typical alcohols include methanol, ethanol, butanol and higher alcohols, whereas typical primary amines include methylamine, ethylamine and higher amines. Reactants with both alcohol and amine groups also can be used, such as ethanolamine. Reactants should be chosen so as to not impair the viability of the cells.

The outer layer of the membrane comprises a biocompatible synthetic polyelectrolyte having a charge opposite that of the biopolymer. Thus, when the biopolymer is polycationic (e.g., modified collagen), the synthetic polyelectrolyte used in the outer layer is polyanionic. Conversely, when the biopolymer is polyanionic (e.g., HA, modified HA, etc.), the synthetic polyelectrolyte used in the outer layer is polycationic. Suitable outer layer synthetic polyelectrolytes form a complex with the oppositely-charged biopolymer to form a membrane by the complex coacervation process and impart stability to the encapsulate. The charge density of the synthetic polymer typically will be from about 0.1% to about 20%, preferably is at least about 1%, and even more preferably is at least about 3%. Like the biopolymers, the synthetic polyelectrolytes preferably have a molecular weight of at least 20,000, preferably at least 75,000, more preferably at least 125,000, even more preferably at least 200,000, and yet even more preferably at least 250,000.

The biocompatible synthetic polyelectrolyte layer that is capable of forming, with the biopolymer of the inner layer, a membrane which allows environmentally-sensitive living cells, such as hepatocyte cells, to remain viable and, at the same time, protects the cells against immunological rejection by the host. A preferred class of biocompatible synthetic polyelectrolytes is acrylate polymers. Such polymers include acrylate polymers, copolymers and ter-polymers such as poly (acrylic acid), poly(methacrylic acid), poly(methacrylate), poly(methyl methacrylate), and acrylate copolymers and ter-polymers of acrylic acid, methacrylic acid, methacrylates, methyl methacrylates, hydroxyethyl methacrylic such as 2-hydroxyethyl methacrylate, hydroxypropyl-acrylate and the like, and blends thereof. Poly(dimethylaminoethyl methacrylate) (DMAEMA) and copolymers and ter-polymers of dimethylaminoethyl methacrylate with 2-hydroxyethyl methacrylate and/or hydroxypropylacrylate and methacrylate and/or methyl methacrylate are preferred cationic synthetic polymers. Copolymers or ter-polymers of acrylic acid and/or methacrylic acid with 2-hydroxyethyl methacrylic and/or hydroxypropylacrylate and methacrylate and/or methyl methacrylate are preferred anionic synthetic polymers. Each has exhibited biocompatibility when used in other biomaterials.

A preferred biocompatible synthetic polyelectrolyte outer layer is an acrylate ter-polymer of methacrylic acid (MAA), hydroxyethyl methacrylate (HEMA), and methyl methacrylate (MMA). The ter-polymer preferably comprises from about 10 mol % to about 30 mol %, more preferably from about 15 mol % to about 25 mol % MAA, from about 10 mol % to about 40 mol %, more preferably from about 20 mol % to about 30 mol % HEMA, and from about 20 mol % to about 60 mol %, more preferably from about 45 mol % to about 55 mol % MMA. In a preferred embodiment of the present invention, the ter-polymer is formed by polymerizing MAA, HEMA, and MMA monomers in about a 1:1:2 molar ratio.

The membrane of the encapsulated cell is selectively permeable. The cells encapsulated in accordance with the invention remain viable because the membrane is permeable to nutrients and other materials necessary to support the normal metabolic functions of the cells. Thus, ionic materials and oxygen, for example, pass through the membrane. The membrane also is permeable to products of the cells, such as hormones, and to metabolic byproducts. Thus, material produced by the cell can pass through the membrane from the interior of the microcapsule. In this way, material produced by the encapsulated cell can be introduced into the blood of a host, or can be introduced into a culture medium in which encapsulated cells are placed.

The membrane permeability essentially precludes entry of immunoglobulins, macrophages, and other immune system agents that cause rejection of cells by the host's immune system. According to a preferred embodiment of the invention, the membrane is impermeable to molecules greater than about 100 kDa, and preferably is impermeable to molecules greater than about 71 kDa. According to another preferred embodiment of the invention, the membrane is permeable to molecules greater than about 60 kDa and impermeable to molecules greater than about 150 kDa.

The composition of the outer layer can be modified to adjust the permeability and transport properties of the membrane. As an example, the permeability of the membrane to typically polar compounds found in biological systems can be increased by incorporating a hydrophilic copolymer, such as poly(2-hydroxyethyl methacrylate) (HEMA) or other hydroxy-containing acrylates, into the polyelectrolyte which forms the outer layer of the membrane. Increasing hydrophobicity of polyelectrolytes tends to cause decreased permeability.

In the preferred MAA/HEMA/MMA ter-polymer, HEMA provides hydrophilicity to render the ter-polymer water-soluble so that the entire encapsulation can be performed in the physiological aqueous buffer without the need for an organic solvent. MMA imparts mechanical strength, toughness, and elasticity to the microcapsules. MAA provides a negative charge to interact with a positively-charged inner layer. The inner layer preferably is an esterified collagen with net positive charge. The balance between the two charged polymers determines the physical characteristics of the microcapsules. Using a 10% ter-polymer and 1.5 mg/ml of modified collagen, for example, microcapsules can be formed having a thin outer layer (~2 μm) and a semi-gel-like inner layer that minimizes impedance to mass transport across the membrane but remain stable as microcapsules for days. The semi-gel-like inner collagen layer is able to provide a "loose" extracellular matrix configuration that mimics the in vivo situation, therefore allowing the microcapsule to maintain higher levels of cell function. These characteristics of the microcapsules that satisfy most requirements for a bioartificial liver-assisted device (BLAD) were achieved through optimization of several parameters.

The permeability of the membrane also can be adjusted by selection of molecular weight or structure of the outer layer so as to preclude molecules having a preselected molecular weight or structure from passing through the membrane. As the molecular weight of the polyelectrolyte is increased, the membrane tends to be more permeable. Larger differences in charge densities between the inner biopolymer and the outer polyelectrolyte also tend to make the membrane more permeable. The mechanical stability of the membrane can be improved by increasing the molecular weight of the polyelectrolyte in the outer layer or by employing monomers in the polyelectrolyte that provide mechanical strength, such as MMA.

The membrane can be formed by complex coacervation by combining drops of a solution of biopolymer containing a cell suspension with a solution of synthetic polymer at physiological or neutral pHs of from about 6 to about 8 so as to avoid adversely affecting the viability of the cells. In such process, the biopolymer is dissolved in a suitable aqueous solvent that will not adversely affect the viable cells. Such solvents are well known and include buffered saline, culture medium and the like. Similarly, the synthetic polyelectrolyte is soluble in and dissolved in a suitable solvent that will not threaten the viability of the cells. Such solvents include aqueous solvents such as buffered saline, culture medium and the like. The solvent used for the biopolymer does not need to be the same solvent used for the synthetic polymer. Mild agitation of the polyelectrolytic solution can be utilized if desired.

In one suitable technique, a substrate polymer solution containing a cell suspension in a suitable diluent such as phosphate buffered saline (PBS) is added dropwise to a receiving solution containing synthetic polyelectrolyte of the opposite charge in PBS at ambient temperature. A cohesive membrane is formed at the interface of the two solutions to provide encapsulated cells. Advantageously, no organic solvent is required and no cross-linking reaction is necessary. Thus, the conditions of encapsulation are especially mild, yielding little cell mortality.

The proper matching of biopolymer and synthetic polyelectrolyte can be readily confirmed. A drop of a solution of biopolymer can be added to a solution of electrolyte. A proper match results in the rapid formation of a microcapsule or membrane by complex coacervation, which can be observed visually. The suitability of a given encapsulate regarding permeability can be readily determined by in vitro tests using standard cell culture media to determine if desired products are secreted, if unwanted immune components are excluded, and if viability of encapsulated cells is suitably maintained.

The concentrations of the polymer solutions, the size of the droplets added to the synthetic polyelectrolyte solution, and the rate at which the substrate polymer solution containing cell suspension is added to the synthetic polyelectrolyte solution can be adjusted to achieve an encapsulating membrane having the desired thickness of layers and desired size. Suitable concentrations for the biopolymer solution and for the synthetic polyelectrolyte solution will vary depending upon the specific polymers and solvents employed, but determination of such concentrations is easily within the skill of the art. While it is not possible to delineate concentrations for all possibilities, the concentration of the biopolymer often will be from about 0.1 to 2% whereas the concentration of the synthetic polyelectrolyte often will be from about 2 to 6%.

The thickness of the inner, substrate polymer layer, will depend on, inter alia, the viscosity of the biopolymer solution and the degree of penetration into the synthetic polyelectrolyte solution achieved by the substrate polymer solution droplets. The degree of penetration is related to the molecular weight of the polyions and the viscosity of the solutions. The thickness of the outer shell may vary over a wide range, depending on the material used (e.g., whether the microcapsule is Type-II, Type-III, or Type-IV as characterized herein) as well as the properties desired for a particular application. The outer shell most often has a thickness of from about 1 to about 20 μm.

The practice of this invention provides microspheres that may range in size from as small as about 30 μm to as large as several millimeters. The larger sizes are most suitable for cells that tend to aggregate such as islet of Langerhans cells and the like.

The number of cells within each microcapsule can be readily controlled and is a function of the density of the cell suspension within the biopolymer. For example, cells in PBS (which may be at densities of $10^3$ to $10^6$ cells per ml) can be mixed with the biopolymer to provide a variety of cell concentrations. Individual microcapsules can contain any desired number of cells, typically ranging from 1 to 200 cells or more. Collagen gel has been observed to exhibit a "skin effect" that is detrimental to mass transport, as a high concentration of collagen leads to gelation. Such "skin effect" is concentration- and temperature-dependent. Extra-cellular matrices like collagen or Matrigel have gelling temperatures of 22-35° C. depending on the concentration of these proteins. At 37° C., where hepatocytes are normally cultured in a bioreactor or transplantation is performed in vivo, the "skin effect" can be most pronounced. Since mass transport is among the most important considerations for the design of bioreactors in BLAD, it is desirable to employ the optimal concentration of collagen such that the "skin effect" is minimized while there still is enough collagen to complex with the synthetic polyanion forming stable microcapsules.

Albumin was used as a model molecule for the permeability optimization of the microcapsules. Albumin (MW ~67,000 Da) is one of the secreted proteins of hepatocytes. It acts as a carrier to bind most metabolic wastes in the liver for removal from the blood. Another major scavenger protein is bilirubin (~10,000 Da), which is smaller than albumin. Albumin was found to be freely permeable to the microcapsules. A known concentration (1% w/v) of albumin was added to collagen and microcapsules were formed. The microcapsules were equilibrated in a culture medium with the same concentration of albumin (1% w/v) at 37° C. for 2 hours to allow a possible "skin effect" to occur. Such equilibration before the permeability measurements is essential for detecting any "skin effect" from the gelling collagen. Pre-equilibration for up to 5 days indicated that the "skin effect" was marginally more pronounced than with the 2 hour pre-equilibration. The albumin released from the microcapsules into the fresh culture medium with no albumin added was thereafter monitored. With 1.5 mg/ml of the modified collagen, most of the encapsulated albumin was released from the microcapsules within 15 minutes. As the concentration of collagen in the microcapsule was increased to 4 mg/ml (~0.4% w/v), the release of albumin was greatly inhibited. For collagen concentration below 1.5 mg/ml, hepatocytes could not be encapsulated, possibly due to insufficient positive charge from the diluted collagen. Therefore, 1.5 mg/ml of modified collagen was used for all other experiments.

One preferred ter-polymer composition is made up of 25 mol % HEMA, 25 mol % MAA and 50 mol % MMA at a concentration of 10% in PBS. When the ter-polymer composition was modified for higher negative charge at the expense of mechanical stability (e.g., 50 mol % MAA, 25 mol % HEMA, 25 mol % MMA), the urea-synthesis of the encapsulated hepatocytes decreases to levels below the monolayer control. The polymer composition and concentrations can be varied to achieve enhanced mechanical stability and other physical characteristics.

Because the membrane of the encapsulated cells of the invention precludes contact between the cells and the host's immune mediators, all types of living cells, including both naturally-occurring and genetically-engineered cells, may be encapsulated. The encapsulates are suitable for anchorage-independent cells and are particularly suitable for encapsulation of environmentally sensitive, anchorage-dependent living cells such as hepatocytes.

Encapsulated cells of the invention also are useful as, for example, a hormone-producing system. Use of cells microencapsulated in a selectively permeable biopolymeric membrane affords the opportunity to provide artificial organs and other methods for improving and restoring functions in people with physical disabilities.

An example of one type of hormone-producing cell is a cell of the anterior pituitary gland. Such cell excretes growth hormone, which inter alia stimulates skeletal growth. In accordance with the invention, encapsulated naturally-occurring anterior pituitary cells are useful in stimulating skeletal growth in a host. The encapsulated cells provide growth hormone produced by the cells and introduced to the blood of a host through the encapsulating membrane. Growth hormone also can be produced by genetically-engineered microorganisms. Such microorganisms, when encapsulated, may be used to provide growth hormone to a host.

Encapsulated cells that secrete hormones also may be suspended in a culture medium and will excrete hormone over an extended period. Encapsulated insulin-producing cells, for example, mammalian pancreatic alpha cells, beta cells, or intact islets of Langerhans, may also be used as an artificial pancreas. Such encapsulated cells can be implanted into a diabetic mammal and will function in vivo to excrete insulin and other hormones in response to host blood glucose concentration.

Other types of cells also may be beneficially encapsulated. For example, encapsulated neurotransmitter-secreting cells may be used to treat neurological disorders such as Parkinson's and Alzheimer's diseases. Similarly, chromaffin cell transplants may be used for alleviation of pain, especially chronic pain, and encapsulated chondrocytes may be used for repair of musculoskeletal defects. Skilled practitioners recognize the utility of encapsulating living cells, and will be able to identify still further cells suitable for encapsulation in accordance with the invention.

Even though the membrane may be permeable to proteases that can digest collagen and other biopolymers used to form the inner layer of the membrane, it has been found that the inner layer remains intact. Without being bound by any theory, it is believed that the proteases cannot digest the modified collagen, HA, modified HA, or other biopolymer when the biopolymer is complexed with the outer layer. This resistance can be analogized to the resistance to solubilization of type I collagen and to cross-linked collagen, such as is found in heart valve tissue. Again, without wishing to be bound by theory, it is postulated that the complexation shields or changes the conformation of the cleavage site (between glycine and leucine), thus making the resulting complexed biopolymer resistant to degradation.

The length of the period during which encapsulated cells remain intact will depend upon the properties of the medium in which the encapsulated cells are used and upon the composition of the biopolymer and of the synthetic polyelectrolyte. For example, encapsulated cells used in a culture medium might be expected to remain intact for a longer period than encapsulated cells introduced into a human or animal body. Also, the mechanical stability of the membrane can be improved by increasing the molecular weight of the synthetic polyelectrolyte. Skilled practitioners will be able to determine the length of the period during which encapsulated cells remain intact in various media.

Much effort on cell micro-encapsulation has focused on the materials and processes that make microcapsules for cell transplantation, cell-based drug delivery, and culture in bioreactors. There are a number of considerations for making microcapsules, but some are more important for certain applications than the others. For example, islet transplantation has more stringent requirements on immune isolation than microencapsulated hepatocyte cultured in an extra-corporeal bioreactor, which requires microcapsules with good mass transfer properties. This is because transplanted islets must function in vivo for extended periods of time, while the latter is often used for a few hours ex vivo. However, there are characteristics such as the good microenvironment for cell viability and functions, and the maximal permeability for oxygen and nutrient supply, which are important for all applications. The present invention provides a multi-layer microcapsule system based on such common characteristics, while allowing the other characteristics to be imparted by the individual layers of the microcapsules.

The four types of microcapsules (Types I-IV) according to preferred embodiments of the invention all share the same inner layer of modified collagen at 1.5 mg/ml. At such low concentration, the modified collagen does not completely gel but surrounds the cells loosely in a semi-gel state. Such a configuration provides a very good microenvironment for cellular functions. For the Type-II, -III, and -IV microcapsules, the additional layers most preferably should minimize the permeability impedance to the innermost layer to maintain good microenvironment for optimal cellular functions.

The four types of microcapsules (Types I-IV) described herein have some degrees of freedom for tuning the critical aspects of the microcapsule performance for different tissue engineering applications: good microenvironment for cellular functions, mechanical stability, complete encapsulation and selective permeability for potentially more reliable immune isolation. Type-I microcapsules provide a good microenvironment for cellular functions and exhibit good mass transfer properties, but are mechanically unstable and cannot ensure complete cell encapsulation. Type-I microcapsules are useful for applications such as the single-use bioreactor of an extra-corporeal device.

Type-II microcapsules have a more thorough cell encapsulation, which might provide a potentially more reliable immune isolation as well as better mechanical stability. Type-II microcapsules are more suitable for short-term applications such as hepatocyte transplantation where the transplanted hepatocytes are intended to stimulate the liver regeneration within a few weeks.

Figure 2A:
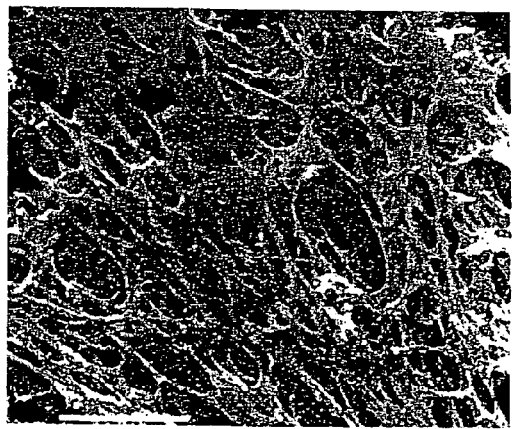
FIGS. 2A and 2B are images of a Type-III microcapsule surface.
Figure 2B:

Type-III and -IV microcapsules provide significantly improved mechanical stability. Mechanical stability can be especially improved by using biocompatible materials such as alumina to form a macro-porous exoskeleton outside Type-I microcapsules. Polymers that carry positive charges, such as chitosan, can complex with the negatively charged ter-polymer shell. The micro-porosity of the exoskeleton layer can be controlled by the concentration of chitosan. As alumina possesses a relatively high point of zero charge (PZC) of 9.0, the particles of alumina sol at the physiological pH (7.2-7.4) possess positive charges. The positive charges on the alumina sol are neutralized by the negatively charged ter-polymer at pH 7.4. Due to this charge neutralization reaction, the alumina particles that originally repel each other due to their mutual positive charges begin to condense, resulting in the formation of a stable, macro-porous alumina network (FIG. 2B). Such an alumina sol-gel exoskeleton can be formed and optimized over a relatively wide range of concentrations. Type-III microcapsules are mechanically very stable over a period of 7 days as measured by nano-indentation assay. These mechanically stable microcapsules are expected to be suitable for culturing cells in a dynamic environment such as a fluidized bed bioreactor for large-scale cell culture or bio-artificial organs.

Type-IV microcapsules have an additional ter-polymer shell outside the exoskeleton of Type-III microcapsules. The negatively charged surfaces may minimize the adsorption of plasma proteins. With the relatively stable exoskeleton covered by a selectively permeable, negatively charged ter-polymer shell, the Type-IV microcapsules with two layers of built-in immune isolation features can allow plasma or even the whole blood to directly contact the microcapsules without the use of a hollow fiber membrane for immune isolation. The Type-IV microcapsules are expected to be useful in bio-artificial liver and in cell transplantation applications.

EXAMPLE

The following example is illustrative of preferred aspects of the invention and should not be construed to limit the scope of the present invention. All reagents were purchased from Sigma-Aldrich unless otherwise indicated.

Ter-Polymer Preparation

Ter-polymer of methacrylic acid (MAA), 2-hydroxyethyl methacrylate (HEMA), and methyl methacrylate (MMA) was synthesized by solution polymerization in 2-propanol using 2,2'-azobisisobutyronitrile (AIBN) as initiator. The monomers were distilled under nitrogen at reduced pressure. The polymerization was performed with an initiator concentration of 0.1 mol % of monomers under nitrogen with a magnetic stirrer at 78° C. in an oil bath. The molar feed ratio of MAA, HEMA, and MMA was fixed at 25:25:50 or other ratios as desired and the ratio of total monomer to solvent at 1:6 (W/V). The reaction was allowed to proceed for overnight and quenched by cooling to room temperature. The polymer was precipitated by addition to a large excess of petroleum ether. The precipitate was re-dissolved in a minimum volume of ethanol, and re-precipitated in distilled water. Recovered polymer then was dissolved in a 1 M sodium hydroxide solution, and further purified by repeated dialysis against distilled water with MWCO of 3500, and lyophilized. The yield of the polymer was found to be 63%. The polymer composition was determined by proton NMR and the molar ratio of MAA, HEMA, and MMA was found to be 20.4:27.4:52.2 for the molar feed ratio of 25:25:50. The molecular weight of the ter-polymer before dialysis was determined by GPC (with THF as eluent) to be 30,000.

Modification of Collagen

Collagen can be modified to be cationic and anionic by the removal of either the negative or the positive charge from the collagen chains. In this case, cationic collagen was obtained through the modification of the carboxyl group by esterification with low molecular weight alcohol. 20 ml of stock solution (3 mg/ml) of collagen (Vitrogen 100, Collagen Corp., Palo Alto, Calif.) was first precipitated with 400 ml of acetone. The precipitated collagen was dissolved in 200 ml of 0.1 M HCl containing methanol (Merck), stirred at 4° C. for 6 days under sterile conditions. The lyophilized modified collagen can then be stored up to 6 months in −20° C. in the presence of desiccant. The modification was monitored by titration. Titration of the natural collagen gave a typical titration curve of a mixed acid or a dibasic acid, while that of modified collagen gave a typical titration curve of a week monobasic acid, indicating that most carboxyl groups have been esterified in modified collagen. In addition, neutralization of the modified collagen needs less sodium hydroxide than that of the natural collagen, indicating that the polymer chain of the modified collagen has less ionic groups because of the esterification of the carboxyl groups.

Isolation of Hepatocytes

Hepatocytes were harvested from male, Wistar rat, weighing from 250-300 g by a 2-step in situ collagenase perfusion. The rat was given 100 U/kg of heparin 30 minutes before anesthesia. Pentobarbital was administered at a dose of 30 mg/kg, intra-peritoneally at the start of the operation. After laparotomy, a portal cannula was placed and fixed in a position along the portal vein. A cut was rapidly made in the lower vena cava. In the first 2-3 minutes, pre-perfusion (with $Ca^{2+}$-free perfusion buffer) was performed while the liver remained in situ. The perfusate flow was started at a rate of 50 ml per minute. While pre-perfusion was carried out, the liver was transferred to a petri-dish and placed in a position similar to its in situ site. After 10 minutes of pre-perfusion with $Ca^{2+}$-free medium, the liver was then perfused with recirculating 0.05% collagenase buffer for another 10 minutes. This was terminated when the vena cava ruptured. The entire perfusion procedure was performed under oxygenation that greatly improved the cell viability. The cells were liberated from the connective vascular tissue and re-suspended in fresh growth medium. This was followed by incubation of the cell suspension in a 37° C. $CO_2$ incubator for 30 minutes. The cell suspension was then filtered through a nylon mesh with a 60-μm pore size to further remove the connective tissue debris. The filtrate was then centrifuged at 50 g for 1 minute to obtain the cell pellet. The cells were collected and washed twice with growth medium. The viability of the hepatocytes was determined to be 90-95% in all cases using the conventional Trypan Blue exclusion test.

Preparation of Exoskeleton Materials

A. Preparation of Alumina Sol

Aluminum sec-butoxide (7.5 ml) was slowly added to 250 ml deionized water at 85° C. The suspension of white precipitate was magnetically stirred for half an hour, after which 0.15 ml of fuming hydrochloric acid (37%) was added to the suspension and kept in a stoppered vessel at 95-100° C. for 3 days. The resulting alumina sol was cooled to room temperature before use. The concentration of sol in term of aluminum (Al) concentration is 0.1168 M. The stock solution is further diluted with PBS to the desired working concentration (0.003 M to 0.006 M) before use.

B. Preparation of Chitosan

A stock solution of 2% chitosan (MW 400,000) was prepared by dissolving in 0.5% acetic acid at 95° C. The final working concentration of 0.01-0.02% was achieved through dilution of the stock with PBS.

Preparation of Microencapsulates

Micro-encapsulation was performed at room temperature with the aid of a syringe pump (IVAC P6000, Alaris Medical Systems, San Diego, Calif.). The microcapsules were incubated at 37° C. for one hour to allow the modified collagen to partially gel harvested by sedimentation and subsequently washed twice with IX Phosphate Buffered Saline (PBS) for further studies (Type-I microcapsules).

Type-II microcapsules were prepared by re-encapsulating the Type-I microcapsules in 1.5 mg/ml of modified collagen solution and 10% ter-polymer solution using the same method as in the Type-I microcapsule preparation.

Type-III microcapsules were prepared by re-suspending the Type-I microcapsules in the respective exoskeleton materials for about 3 minutes for the formation of a macro-porous network, followed by extensive washing in PBS before in vitro culture.

Type-IV microcapsules were prepared by re-encapsulating the Type-III microcapsules in a 10% ter-polymer solution.

In Vitro Culture

The microcapsules were cultured for the required amount of time in Hepatozym Serum free medium (SFM, GIBCO Laboratories, Chagrin Falls, Ohio) in a 35 mm polystyrene dish in a humidified atmosphere with 5% $CO_2$. The culture medium was supplemented with $10^{-7}$ M dexamethasone, 10 nM insulin (Boehringer Mainnhem), 20 ng/ml epidermal growth factor and 1% Penicillin and Streptomycin. After 1 day of culture, the microcapsules were incubated in the medium with 1 mM of NH$_4$Cl for 90 minutes before the medium was collected for urea assay. The microcapsules were then cultured in fresh medium again.

Functional Analysis of the Microencapsulated Hepatocytes

The samples collected at each time point were assayed for the urea production calorimetrically with the Urea Nitrogen Diagnostic kit (Sigma Diagnostic). Data from three independent encapsulation experiments were analyzed and normalized against 10$^6$ cells.

Permeability Assay for the Microcapsules

Bovine serum albumin (BSA) was suspended in 1.5 mg/ml of modified collagen solution to reach a final concentration of 1% (w/v) and microcapsules of the four types (I-IV) were formed as previously described. The microcapsules were incubated at 37° C. for one hour for the gelation of the collagen. After the incubation, the microcapsules were transferred to a 2 ml PBS solution containing equal concentration of BSA, and allowed to equilibrate for 2 hours. The microcapsules were then washed with PBS and the BSA release profile over a 2-hour interval was obtained. BSA level was determined using the Detergent Compatibility (DC) protein assay (Bio-Rad Laboratories). The percentage of released BSA in PBS was plotted over time with respect to the BSA standards.

Light Microscope Imaging of the Microcapsules

The microcapsules were visualized in an inverted microscope (Olympus CK40, Tokyo, Japan) with phase-contrast optics. The numbers of hepatocytes within microcapsules were counted with the aid of a hemocytometer (Fuchs-Rosenthal).

An Olympus FLUOVIEW confocal microscope was used to image the ter-polymer and the encapsulated hepatocytes in transmitted mode. The thickness of the ter-polymer shell was measured with the software associated with the Olympus FLUOVIEW confocal microscope.

Scanning Electron Microscopy (SEM)

The microcapsules were fixed with 3% glutaraldehye on a coverglass coated with poly-L-lysine for an hour after which they were washed gently with 1×PBS for 5 minutes. The microcapsules were then post-fixed with osmium tetra-oxide for 1 hour and dehydration was accomplished using a graded series of ethanol (25%, 50%, 75%, 95%, and 100%). The microcapsules were then critical point dried for about 2 hours in absolute alcohol and mounted onto an aluminum stub and sputter coated with gold before viewing under a scanning electron microscope (Joel 5600 LV).

Assessment of Mechanical Stability by Nano-Indentation

Indentation measurement was done using a UMIS-2000 Nano-indenter (Australian Scientific Instruments). The three-faced pyramid indenter tip with an inclusion angle of 90° has well-defined geometry that enables the quantitative measurements of the mechanical properties located on the outermost shell or membrane of interest. The load and depth of penetration were measured by two LVDT (Linear Variable Differential Transformer) sensors independently. From the experimentally determined load-penetration data, hardness and modulus were determined through the following analysis:

$$H = P/A$$

$$E/(1-v^2) = (\pi^{1/2})/2 \cdot A^{-1/2} \cdot dP/dh$$

where H is hardness of the specimen, P is indentation load, A is the true contact area at the maximum load, E is the elastic modulus of the microcapsules, and v is Poisson's ratio. dP/dh (called unloading stiffness) essentially is the slope of unloading portion of the indentation load penetration data at the maximum indentation load. Average pressure that the microcapsules can withstand under a sharp point can be defined by applied load divided by contact area. The area of the indentation is therefore related to the depth of penetration, for an ideal sharp Berkovich indenter, is:

$$A = 24.56 h^2$$

Microcapsules of various types were added onto a 13 mm coverglass coated with poly-L-lysine. The elastic modulus and hardness of the microcapsules were determined in the nano-indentation experiments with the maximum load of about 0.15 mN. This gave the penetration depth into the polymer of slightly less than 2 pm before rupture at day 7 for the Type-I microcapsule. The load was applied through a piezoelectric actuator in 15 steps to the maximum load. For each type of microcapsule, an average of 15 microcapsules were indented at the same load for each experiment. Data from three experiments were collected, with one indent on each microcapsule.

Results

Type-I microcapsules were developed with good microenvironment for enhanced cellular functions. Further development of other types of microcapsules should also maintain such a good microenvironment. To accomplish this, a semi-gel-like inner collagen layer (~1.5 mg/ml) should surround the cells to provide a "loose" extra-cellular matrix configuration that mimics the in vivo situation. In Type-I microcapsules, the positively charged collagen layer was encapsulated by a thin layer (2-5 μm) of the negatively charged 10% ter-polymer shell. Other layers were added for specific applications with minimal additional thickness to avoid adverse effects to the functions of the microencapsulated cells.

Type II Microcapsules

Type-I microcapsules typically have a 2-5 μm thin shell, which does not ensure complete cell encapsulation. Like other single-shell microcapsules, the Type-I microcapsules have occasionally been observed with cells protruding out of the microcapsules (FIG. 1). To improve the reliability of immune isolation of the live cells within the microcapsules that are required for many applications, a two-step encapsulation method was employed. To ensure minimal impedance of the mass transfer properties and the functions of the encapsulated cells, the flow rate in the syringe pump was optimized such that the desired minimal thickness of the additional layers was achieved as measured by the confocal imaging. These particular Type-II microcapsules have four separate layers (two ter-polymer shells spaced by the two layers of the modified collagen) with the additional layers covering the protruding cells (FIG. 1) for a potentially more reliable immune isolation than the Type-I microcapsules.

Type III Microcapsules

Type-I microcapsules can maintain structural integrity in static cell culture vessels for a few days. The mechanical stability of the microcapsules requires further improvement for some applications, such as the more dynamic environment in a bioreactor. Therefore, it would be desirable to employ suitable materials that can form highly porous, but mechanically stable, layer(s) outside Type-I microcapsules. It is believed that such outer layer(s) could behave like an exoskeleton to confer mechanical stability while imposing no or little impedance to mass transfer properties of the microcapsules. Ideally, such an exoskeleton should be formed by complex coacervation to avoid exposure of live cells to organic solvents. Therefore, the exoskeleton materials should have net positive charge to interact with the negatively charged ter-polymer shell of the Type-I microcapsules.

Alumina and chitosan were tested for the ability to form macro-porous exoskeleton as examined by SEM. Such microcapsules with macro-porous exoskeleton are referred to herein as Type-III microcapsules. Chitosan can form a macro-porous exoskeleton outside Type-I microcapsules when used in a range of about 0.01-0.02% (w/v) (FIG. 2A). Lower concentrations of chitosan below this range were found not to afford sufficient material to cover the entire microcapsule surface. Higher concentrations of chitosan above this range were found to possess so much positive charges that the Type-I microcapsules disintegrated upon contact. Alumina sol also can form a macro-porous exoskeleton outside Type-I microcapsules when used in a range of about 3-6 mM (FIG. 2B).

Type IV Microcapsules

Figure 3:
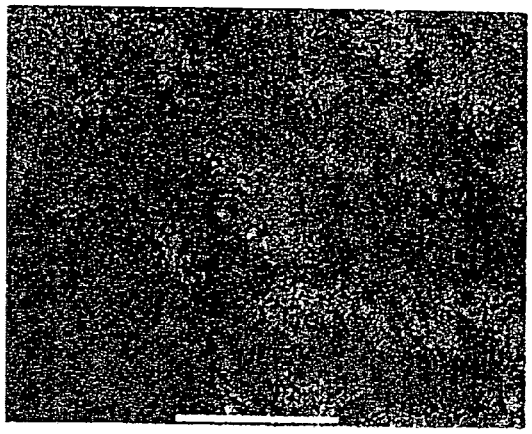
FIG. 3 is a scanning micrograph of a Type-IV microcapsule illustrating that the additional thin layer of ter-polymer resulted in a relatively smooth fourth layer that was sufficient to cover the exoskeleton beneath (scale bars represent 10 μm)

As many plasma proteins, such as serum albumin, are negatively charged (with pI<7) under physiological pH, some applications involving contact with blood would require a negatively charged outer-shell to minimize non-specific protein adsorption onto the microcapsules. Since Type-III microcapsules have a positively charged exoskeleton on the surface, another thin (2-5 μm) layer of the negatively charged ter-polymer shell can be formed outside the exoskeleton by complex coacervation. These Type-IV microcapsules have a selectively permeable, smooth and micro-porous fourth layer (FIG. 3) to ensure complete cell encapsulation for a potentially more reliable immune isolation than the Type-III microcapsules.

Permeability Profile of the Microcapsules

Figure 4:
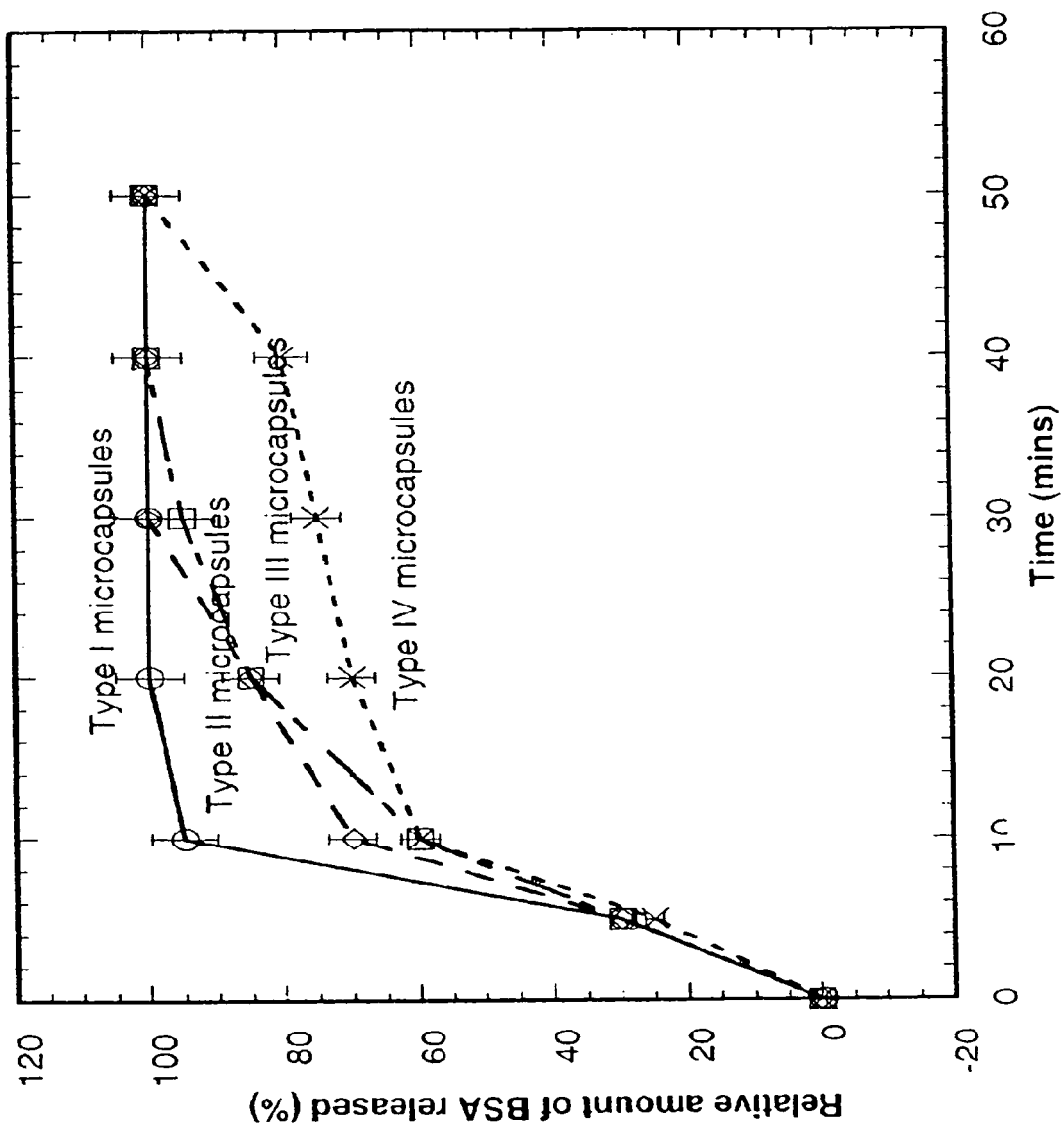
FIG. 4 is a permeability profile of the microcapsules: BSA (1%) was loaded into the four types of microcapsules and the rate of BSA released from the microcapsules was measured (Type-I: (○), Type-II: (□), Type-III: (x), Type-IV: (◊))

For all applications, the microcapsules need to be permeable to nutrients, oxygen and metabolic wastes. Some applications require selective permeability to allow nutrient exchange and at the same time to prevent the passage of large molecules, such as immunoglobulins, into the microcapsules. The permeability profiles of the Type-I, -II, -III, and -IV microcapsules were characterized to assess and optimize the suitability of different types of microcapsules for use in relevant applications. BSA with a MW of 66 kDa was encapsulated inside the microcapsules and the rate of release from the microcapsules was measured by spectrophotometry. Type-I microcapsules (○) were used as a control since they release almost all the encapsulated BSA within 15 minutes (FIG. 4). Type-II (□), Type-III (x), and Type-IV (◊) microcapsules all exhibited some degrees of reduction in permeability. Within about 15 minutes, Type-II microcapsules (□) had about 80% of the BSA released, while Type-III (x) and Type-IV (◊) microcapsules had about 65% of the BSA released. By about 30-50 minutes, almost all the encapsulated BSA was released from all the microcapsules. Since Type-I microcapsules are impermeable to molecules larger than about 150 kDa, the other types of microcapsules should also be impermeable to larger molecules, such as immunoglobulins, which mediate the immune response.

Functional Profiles of the Microcapsules

Figure 5:
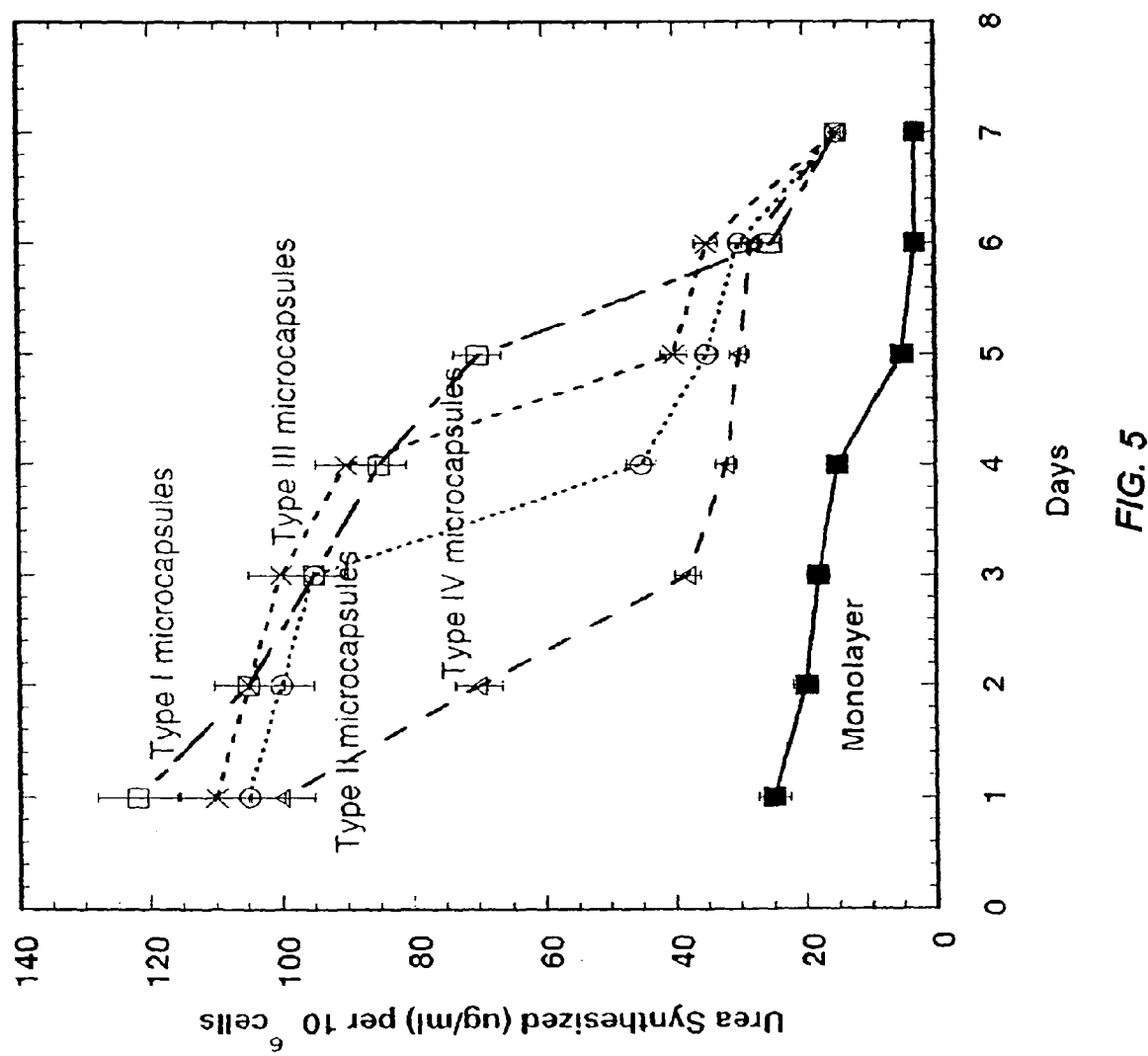
FIG. 5 illustrates a urea production profile of microencapsulated hepatocytes in Type-I (□), Type-II (Δ), Type-III (x), and Type-IV (○) microcapsules, as well as a monolayer control (■).

As Type-II (□), Type-III (x), and Type-IV (◊) microcapsules exhibited some degrees of permeability reduction (FIG. 4) when compared to Type-I microcapsules (○), it is important to investigate the effects of permeability reduction on the functional status of the microencapsulated cells. The urea production profiles of the microencapsulated hepatocytes, which are very sensitive to the extra-cellular microenvironment, were characterized. All four types (I-IV) of microcapsules were found to exhibit similar levels of hepatocyte functions on day 1 (which is defined as 24 hours after the initial cell encapsulation) (FIG. 5). From day 1 onward, the urea production by the Type-II (Δ), Type-III (x), and Type-IV (○) microcapsules decreased one after another from the level exhibited by the Type-I (□) microcapsules. The urea production by the Type-II microcapsules (Δ) started decreasing from day 1 to about 40% of Type-I microcapsules (□) on day 3 and then stabilized from day 3 onwards. The urea production by Type-III microcapsules (x) started decreasing from day 4 to about 50% of Type-I microcapsules (□) on day 5. The urea production by Type IV microcapsules (○) decreased from day 3 to about 45% of Type-I microcapsules (□) on days 4-5. On days 6 and 7, all four types of the microcapsules exhibit similar levels of hepatocyte function, which is approximately the initial level of the monolayer control (■).

Mechanical Stability of the Microcapsules

Type-III and -IV microcapsules were developed to improve mechanical stability. Nano-indentation with a pyramidal indenter tip with an inclusion angle of 90° was used to characterize the mechanical stability of the microcapsules over a period of 7 days (Table 1). Under the 0.15 mN load, which is the maximum load at rupture for Type-I microcapsules for the pyramidal indenter, the depth of penetration into Type-I microcapsule shell increases rapidly from 0.4±0.1 μm on day 1 to 0.6±0.1 μm on day 2 and 1.4~0.8 μm on day 7. The depth of penetration of the pyramidal indenter tip into Type-II and Type-III microcapsule shells remained relatively stable, in the range of 0.4±0.1 μm to 0.6±0.1 μm, throughout the 7-day period. There is a large variation in the depth of penetration of the pyramidal indenter on day 7, which was not observed on days 1 and 2, or in any other types of microcapsules. The protruding cells not encapsulated by the ter-polymer shell might have contributed to such a large variation. The additional layers of either the ter-polymer shell or the exoskeleton could then stabilize Type-II and -III microcapsules over the 7-day period as compared to Type-I microcapsules.

TABLE 1

| | Depth of Penetration (μm ± standard error of means) | | |
|---|---|---|---|
| Days | Type-I Microcapsules | Type-II Microcapsules | Type-III Microcapsules |
| 1 | 0.4 ± 0.1 | 0.4 ± 0.1 | 0.4 ± 0.1 |
| 2 | 0.6 ± 0.1 | 0.4 ± 0.1 | 0.6 ± 0.1 |
| 7 | 1.4 ± 0.8 | 0.5 ± 0.1 | 0.4 ± 0.1 |

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A multi-layer microcapsule comprising bioactive cells attached to a microcapsule membrane; wherein said microcapsule membrane comprises (i) a first inner layer of biopolymer selected from the group consisting of cationic collagen, anionic collagen, anionic esterified hyaluronic acid, anionic amine-modified hyaluronic acid, fibronectin, and laminin; (ii) a second intermediate layer of polyelectrolyte synthetic polymer; and (iii) a third outer layer forming an exoskeleton to provide mechanical stability; wherein said first inner layer and said second intermediate layer are complexed via ionic charges; wherein said second intermediate layer and said third outer layer are complexed via ionic charges; wherein said microcapsule membrane is permeable to molecules smaller than or equal to the size of albumin, to nutrients necessary to sustain normal metabolic functions of the bioactive cells, and to toxins released by the bioactive cells; and wherein said microcapsule membrane is impermeable to immunoglobulins and macrophages.

2. The multi-layer microcapsule of claim 1 wherein said second intermediate layer of polyelectrolyte synthetic polymer is an acrylate ter-polymer of methacrylic acid, hydroxyethyl methacrylate, and methyl methacrylate.

3. The multi-layer microcapsule of claim 1 wherein said third outer layer comprises a material selected from the group consisting of alumina, alumina sol, and chitosan.

4. The multi-layer microcapsule of claim 1 wherein said bioactive cells comprise a mixture of dividing cells and non-dividing cells.

5. The multi-layer microcapsule of claim 4 wherein said bioactive cells comprise a mixture of hepatocyte cells and non-parenchymal cells.

6. The multi-layer microcapsule of claim 1 further comprising (iv) a fourth outer layer comprising a polyelectrolyte synthetic polymer surrounding said third layer, wherein said fourth outer layer is complexed with said third layer via ionic charges.

7. A method of preparing a microcapsule having anchorage-dependent cells surrounded by an inner extracellular matrix and a macro-porous exoskeleton surrounding and supporting the extracellular matrix, the process comprising: preparing an inner extracellular matrix having an inner layer and an outer layer, comprising extruding an inner layer biopolymer solution containing bioactive cells into a biocompatible synthetic polyelectrolyte outer layer; wherein said inner layer and said outer layer have charges sufficient to form a complex of said biopolymer and said polyelectrolyte; and suspending said inner extracellular matrix containing said cells in an exoskeleton material having a charge opposite to that of the outer layer of said extracellular matrix to form a macro-porous exoskeleton over said extracellular matrix.

8. The method of claim 7 wherein said macro-porous exoskeleton comprises at least one of alumina, alumina sol, and chitosan.

9. The method of claim 7 further comprising forming an outer shell by encapsulating the microcapsule in a synthetic polymer solution.

10. The method of claim 9 wherein said synthetic polymer solution comprises an acrylate ter-polymer of methacrylic acid, hydroxyethyl methacrylate, and methyl methacrylate.

11. A microcapsule for culturing anchorage-dependent cells comprising an inner extracellular matrix surrounding cells, a macro-porous exoskeleton surrounding and supporting the extracellular matrix; and an outer shell of synthetic polymer surrounding the macro-porous exoskeleton; wherein said microcapsule is permeable to nutrients necessary to sustain normal metabolic functions of the cells and to toxins released by the cells; and wherein said outer shell has a thickness of from about 1 to about 20 $\mu$m.

12. The microcapsule of claim 11 wherein said inner extracellular matrix comprises a biopolymer inner layer and a biocompatible synthetic polyelectrolyte outer layer, wherein said inner layer and said outer layer have charges sufficient to form a complex of said biopolymer and said polyelectrolyte.

13. The microcapsule of claim 11 wherein said macro-porous exoskeleton comprises at least one of alumina, alumina sol, and chitosan.

14. The microcapsule of claim 11 wherein said synthetic polymer of said outer shell comprises an acrylate ter-polymer of methacrylic acid, hydroxyethyl methacrylate, and methyl methacrylate.

15. A process of preparing a bioartificial liver assist device comprising encapsulating one or more hepatocytes within a microcapsule of claim 11, and packing one or more hepatocyte-containing biocompatible microcapsules in a bioreactor.

16. A bioartificial liver assist device comprising one or more of the biocompatible microcapsules of claim 11 contained within a bioreactor, wherein hepatocytes are encapsulated within the one or more biocompatible microcapsules.

17. A method of preparing living cells for multi-dimensional imaging to study cells, tissue, or tissue constructs, the method comprising culturing at least one cell in the microcapsule of claim 11 and imaging the cell using microscopy.

18. A method of preparing living cells for transplantation comprising culturing at least one cell in the microcapsule of claim 11, harvesting the cell, and coupling the cell to a scaffold.

19. A method of analyzing cells comprising removing at least one cell from a biopsy sample, culturing the cell in the microcapsule of claim 11, and performing cytometry analysis.

* * * * *